United States Patent [19]

Furukawa et al.

[11] Patent Number: 5,451,520
[45] Date of Patent: Sep. 19, 1995

[54] CREATINE AMIDINOHYDROLASE FROM ALKALIGENES SP. KS-85 FERM BP-4487

[75] Inventors: Keisuke Furukawa; Kyoko Hashimoto; Masaru Suzuki, all of Noda, Japan

[73] Assignee: Kikkoman Corporation, Japan

[21] Appl. No.: 343,972

[22] Filed: Nov. 18, 1994

[30] Foreign Application Priority Data

Dec. 17, 1993 [JP] Japan .................................. 5-318675

[51] Int. Cl.$^6$ .......................... C12N 9/78; C12N 1/12; C12N 1/00
[52] U.S. Cl. ................................. 435/227; 435/829; 435/252.1
[58] Field of Search .................... 435/227, 829, 252.1

*Primary Examiner*—David M. Naff
*Assistant Examiner*—Michael Meller
*Attorney, Agent, or Firm*—Finnegan, Henderson, Farabow, Garrett & Dunner

[57] ABSTRACT

A creatine amidinohydrolase with the following physicochemical properties is prepared:
(a) action: hydrolysis of 1 mole of creatine to form 1 mole of sarcosine and 1 mole of urea;
(b) substrate specificity: specific for a creatine substrate;
(c) optimum pH: 7–9;
(d) optimum temperature: around 35°–45° C.;
(e) pH stability: stable in the range of pH 5.0–10.5 at 25° C. for 17 hours;
(f) thermal stability: stable at a temperature up to about 45° C. at pH 7.5 for 30 min.;
(g) inhibitors: $AgNO_3$, $HgCl_2$, $CuSO_4$, etc.; and
(h) molecular weight: about 80,000±5000 as determined by gel filtration.

The creatine amidinohydrolase is stable in high pH range and possesses a small Km value, so that it can be purified in high pH range resulting in more easy and simple production than the conventional enzyme, and the lower Km value enables reduction in the period of time and in the amount of the enzyme for each measurement. The creatine amidinohydrolase is obtained by culturing Alkaligenes sp. KS-85 FERM BP-4487.

2 Claims, 3 Drawing Sheets

—□— 50 mM SODIUM ACETATE-HYDROCHLORIC ACID BUFFER
—■— 50 mM PHOSPHATE BUFFER
—▲— 50 mM TRIS-HCl BUFFER

—□— 50 mM SODIUM ACETATE-HYDROCHLORIC ACID BUFFER
—●— 50 mM PHOSHATE BUFFER
—▲— 50 mM TRIS-HCl BUFFER
—✶— 50 mM GLYCINE-NaOH BUFFER
—△— 50 mM CAPS BUFFER

CREATINE AMIDINOHYDROLASE FROM ALKALIGENES SP. KS-85 FERM BP-4487

FIELD OF THE INVENTION

The present invention relates to novel creatine amidinohydrolase and a process for producing the same.

BACKGROUND OF THE INVENTION

It is known that creatine and creatinine present in human serum or urine serve as indicators for the diagnosis of human diseases, particularly kidney disorders.

As an essential method for the chemical quantification of the above substances, the Jáffe method has been known up to now, but presents disadvantages such as troublesome procedures, low specificity, etc. Under these circumstances, a method for the enzymatic quantification of creatinine and/or creatine has been developed. In this method, creatinine is hydrolyzed by creatinine amidinohydrolase to form creatine which in turn is hydrolyzed into sarcosine and urea by creatine amidinohydrolase, and finally sarcosine oxidase is allowed to act on the resulting sarcosine so that the creatinine is quantitatively determined. Recently, this method is rapidly prevailing in clinical examination owing to the easy and simple procedures and higher specificity than that of the above chemical method.

The above creatine amidinohydrolase is known from e.g. Japanese Patent Publication No. 76,915/91.

However, such conventional creatine amidinohydrolase has disadvantages such as difficult purification at pH 8.5 or higher owing to its narrow stable pit range 4.5-8.5 and the long period of time required for the measurement of a sample owing to its high Km value.

SUMMARY OF THE INVENTION

The object of the present invention is to provide creatine amidinohydrolase of lower Km value stable in high pH range.

As a result of their screening for a microorganism having the ability to produce novel creatine amidinohydrolase free from the above disadvantages, the present inventors found that one bacterial strain belonging to the genus Alkaligenes separated from soil produces creatine amidinohydrolase free from the above disadvantages.

That is, the present invention relates to novel creatine amidinohydrolase with the following physicochemical properties:

(a) action: hydrolysis of 1 mole of creatine to form 1 mole of sarcosine and 1 mole of urea;
(b) substrate specificity: specific for a creatine substrate;
(c) optimum pH: 7-9;
(d) optimum temperature: around 35°-45° C.;
(e) pH stability: stable in the range of pH 5.0-10.5 at 25° C. for 17 hours;
(f) thermal stability: stable at a temperature up to about 45° C. at pH 7.5 for 30 min.;
(g) inhibitors: $AgNO_3$, $HgCl_2$, $CuSO_4$, etc.; and
(h) molecular weight: about 80,000±5000 (gel filtration).

The present invention further relates to a process for producing novel creatine amidinohydrolase comprising culturing a microorganism belonging to the genus Alkaligenes capable of producing the creatine amidinohydrolase in a medium and recovering said creatine amidinohydrolase from the culture.

DETAILED DESCRIPTION OF THE INVENTION

Figure 1:
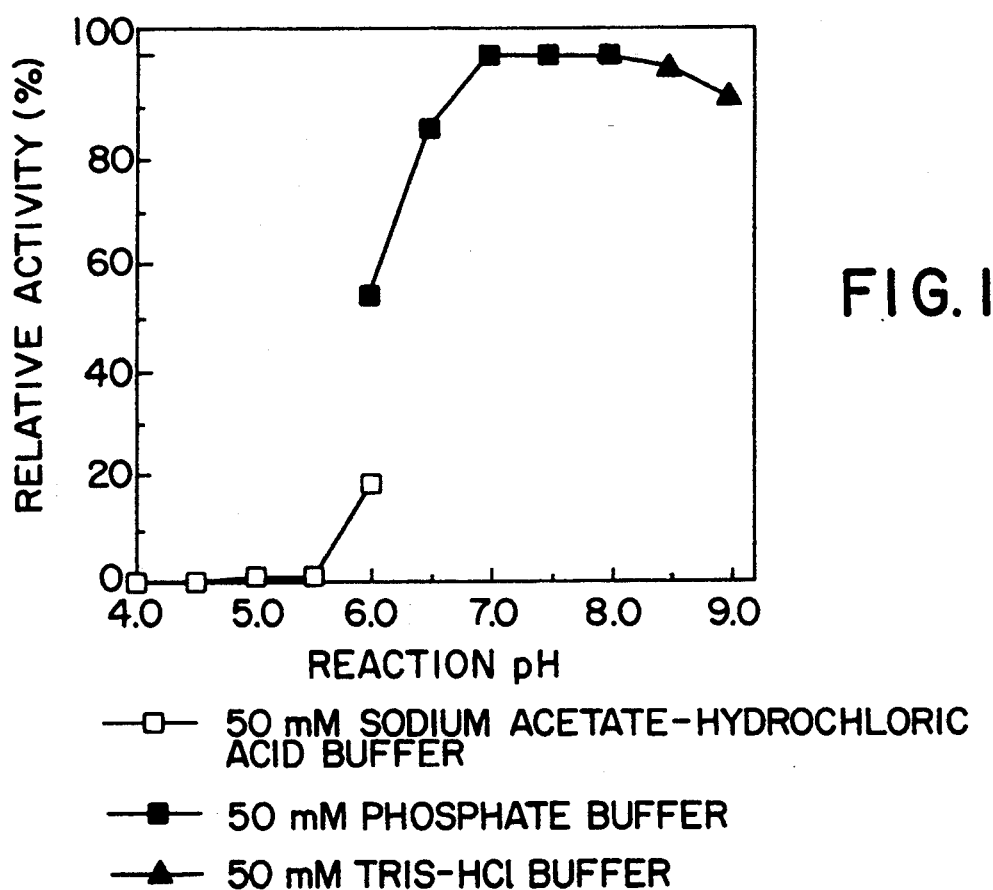
FIG. 1 is a graphic depiction of the optimum pH of the present enzyme. The amount of urea formed by the enzyme reaction was determined, using measurement conditions for each buffer and each pH of 37° C. and 10 minutes.
Figure 2:
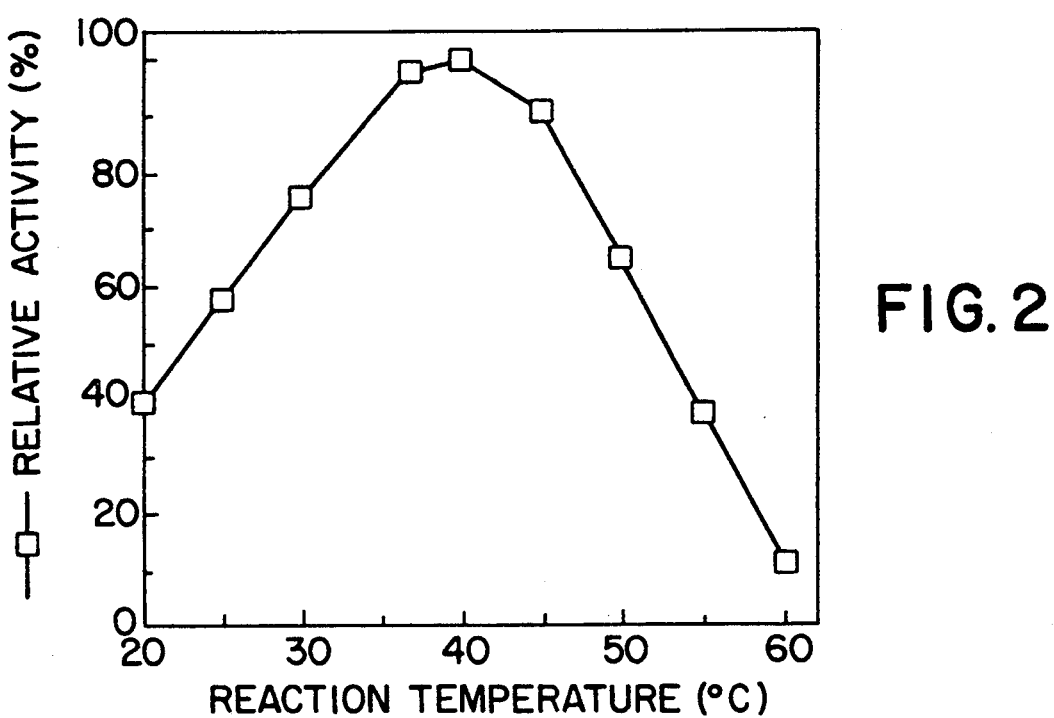
FIG. 2 is a graphic depiction of the optimum temperature of the present enzyme. The amount of urea formed by the enzyme reaction was determined, using activity measurement conditions at each temperature of 50 mM phosphate buffer and pH 7.7 for 10 minutes.
Figure 3:
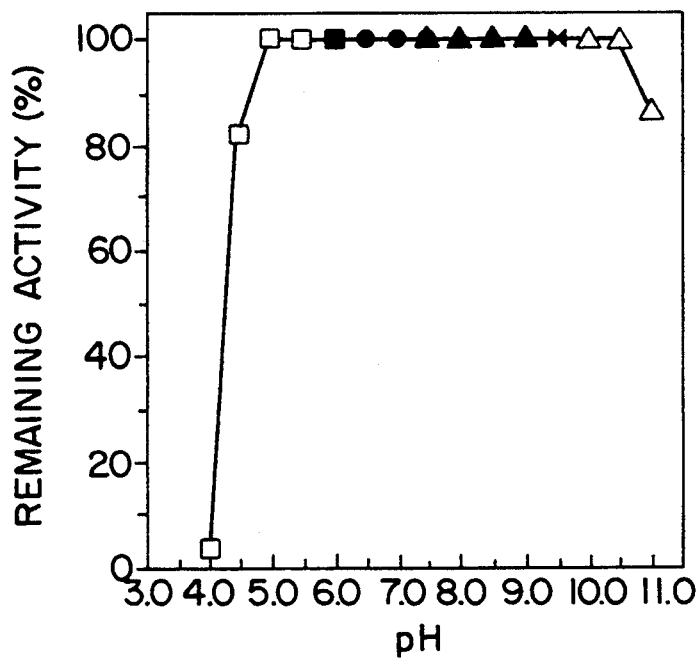
FIG. 3 is a graphic depiction of the pH stability of the present enzyme under treatment conditions for each pH of 25° C. for 17 hours.
Figure 4:
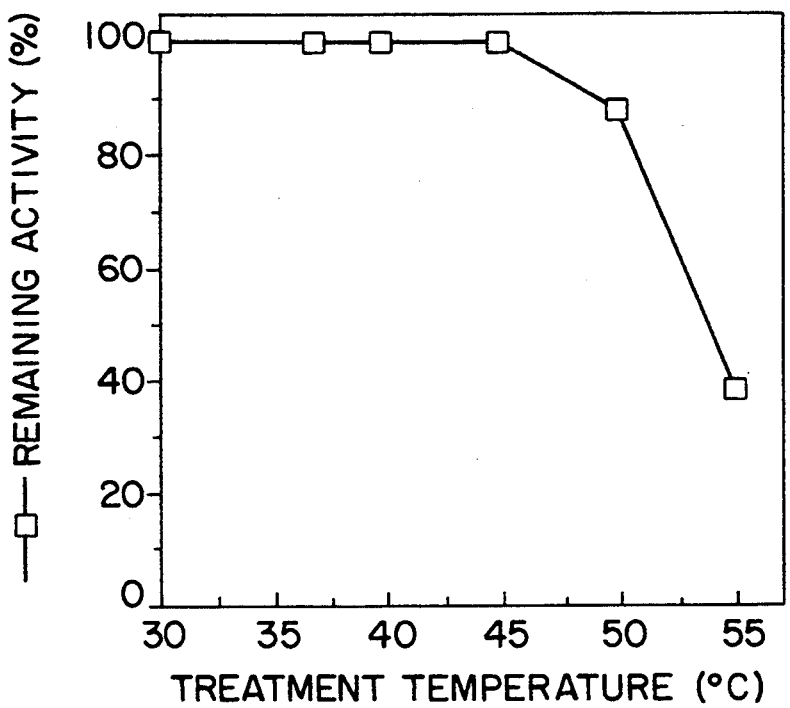
FIG. 4 is a graphic depiction of the thermal stability of the present enzyme. The amount of urea formed by enzyme reaction was determined under the treatment conditions of 50 mM Tris-HCl buffer at pH 7.5 for each temperature for 30 minutes and the measurement conditions of 50 mM phosphate buffer at pH 7.7 and 37° C. for 10 minutes.

The bacterial strain for use in the production of the novel creatine amidinohydrolase of the present invention (hereinafter referred to as "the present enzyme") may be any of the microorganisms belonging to the genus Alkaligenes and having the ability to produce the present enzyme, or may be any variant or mutant thereof.

A specific example of microorganism is Alkaligenes sp. KS-85.

The Alkaligenes sp. KS-85 strain, newly obtained by screening from soil in Kyoto Prefecture, possesses the following bacterial properties. The experiments for the identification of the bacterial properties were conducted on the basis of "Biseibutusu No Bunrui To Dotei" (Classification and Identification of Microorganisms), edited by Takeji Hasegawa and published by the Tokyo University Press (1975). For classification and identification, reference was made to Bergey's Manual of Determinative Bacteriology, 8th edition (1974).

Bacterial properties of Alkaligenes sp. KS-85

(A) Morphological Features

Observed under a microscope (24- to 48-hour culture at 30° C. on meat agar medium, pH 9.0).

(1) cell shape and size: rod-shaped bacillus of 0.5–1.0×0.5–4.0 micron.
(2) motility: motile with surrounding pipi.
(3) spore: absent.
(4) Gram stain: negative.
(5) resistance to acidity: negative.

(B) Growth States In Each Medium (pH 8.0)

(1) meat agar plate culture:
Culture at 30° C. for 5 days indicates the formation of pale yellow round colonies of 2–3 mm diameter. The surface is smooth with fat-like gloss and the outside is transparent (white with pale yellow).
(2) meat agar slant culture:
Stationary culture at 30° C. for 9 days indicates dispersing growth. The color of the microorganism is beige and no pigment is formed.
(3) meat liquid culture:
Stationary culture at 30° C. for 9 days indicates filmy growth on the liquid medium with precipitates formed on the bottom.
(4) meat gelatin culture:
Stationary culture at 20° C. for 30 days indicates growth on only the surface of the medium without liquefying the gelatin.
(5) litmus milk
Stationary culture at 30° C. for 9 days indicates no solidification or liquefaction of the litmus milk, with a rise in the pH of the medium due to the alkali produced in the medium.

(C) Physiological Properties

Examined in a medium adjusted to pH 6.5 or thereabout.
(1) nitrate reduction: no reduction.
(2) denitrification: absent.
 (formation of nitrite under aerobic conditions).
(3) MR test: negative.
(4) VP test: negative.
(5) indole formation: no formation.
(6) hydrogen sulfide formation: no formation.
(7) starch hydrolysis: no hydrolysis.
(8) citric acid utilization: not utilizing.
(9) utilization of inorganic nitrogen sources: not utilizing
 (nitrate and ammonium salt).
(10) pigment formation: no formation.
(11) urease: negative.
(12) oxidase: positive.
(13) catalase: positive.
(14) growth range: temperature; 15°–45° C., pH; 6.0–9.0.
(15) attitude toward oxygen: aerobic.
(16) O–F test (Hugh-Leifson method): no oxidation or fermentation(17) acid and gas formation from sugars: none (the sugars examined are L-arabinose, D-xylose, D-glucose, D-mannose, D-fructose, D-galactose, malt sugar, sucrose, lactose, trehalose, D-sorbitol, D-mannitol, inositol, glycerin, and starch).

From the above bacterial properties, the present bacterial strain was identified as belonging to the genus Alkaligenes, and thus it was designated Alkaligenes sp. KS-85. The present bacterial strain has been deposited under FERM BP-4487 with the National Institute of Bioscience and Human-Technology, Agency of Industrial Science and Technology, Japan.

For the production of the present enzyme, the above bacterial strain is cultured preferably in a liquid medium containing creatine or creatinine. Any conventional culture medium may be used for the production of the present enzyme. As the nitrogen source, mention is made of any utilizable nitrogen compound including creatine, creatinine, yeast extract, peptone, meat extract, corn steep liquor, soybean powder, amino acids, ammonium sulfate, ammonium nitrate, or the like. As the carbon source, mention is made of any assimilable carbon compound including creatine, creatinine, molasses, or the like. As the additional ingredients, mention may be made of a wide variety of salts such as sodium chloride, potassium chloride, magnesium sulfate, manganese chloride, ferrous sulfate, potassium phosphate, potassium dihydrogenphosphate, etc., vitamins, antifoaming agents, etc. The nutrient sources may be used singly or in combination.

For the production of the present enzyme in a liquid medium prepared as described above, aerobic culture such as submerged spinner culture under aeration or spinner culture is preferable. For such aerobic culture, the initial pH of the medium is adjusted in the range of 6.5–7.0, and culture is continued for 24 hours or more at a temperature of 25°–37° C., preferably around 30° C. After conclusion of the culture, the present enzyme can be recovered from the culture by any conventional method for enzyme recovery.

It is desirable that the microorganism is separated from the culture by e.g. filtration, centrifugation, etc., and then washed before the recovery of the present enzyme, because a major portion of the present enzyme is accumulated in the bacterial body. In this case, it is preferable that the bacterial body is disrupted by ultrasonication, French press, dynomill, etc., or the cell wall is lysed with a cell wall-lysing enzyme such as lysozyme, or otherwise the present enzyme is extracted from the bacterial body with a surface-active agent such as Triton X-100 or the like, although the enzyme may be recovered from the intact bacterial body.

The isolation of the present enzyme from the crude enzyme thus obtained may be effected by any conventional enzyme purification method. For example, it is preferable to use a suitable combination of salting out with ammonium sulfate, precipitation with organic solvent, ion-exchange chromatography, gel filtration chromatography, absorption chromatography, electrophoresis, etc.

The present enzyme can be employed for the quantitative determination of creatine in human serum or urine as a diagnosis reagent for a wide variety of diseases including kidney disease.

The present enzyme possesses the following enzymatic and physicochemical properties:
(1) Action: hydrolysis of 1 mole creatine to form 1 mole of sarcosine and 1 mole of urea.
(2) Substrate specificity: specific for the substrate creatine.
(3) Optimum pH:
The optimum pH of the present enzyme was found to be in the range of pH 7.0–9.0 as shown in Table 1 in which the activity of the present enzyme at each pH was determined in 50 mM sodium acetate-hydrochloric acid buffer (pH 4.0–6.0), 50 mM phosphate buffer (pH 6.0–7.5) and 50 mM Tris-HCl buffer (pH 7.5–9.0).
(4) Optimum temperature:
The optimum temperature of the present enzyme was found to be in the range of 35°–45° C. as shown in Table 2 in which the activity of the present enzyme at each temperature was determined using a reaction solution described below in the item "enzyme activity measurement".

(5) pH stability:

The stable pH range was in pH 5.0–10.5 as shown in Table 3 in which the remaining activity of the present enzyme was determined after being allowed to stand at each pH between 4.0–11.0 at 25° C. for 17 hours. The buffers used were in 50 mM sodium acetate-hydrochloric acid buffer (pH 4.0–6.0), 50 mM phosphate buffer (pH 6.0–8.0), 50 mM Tris-HCl buffer (pH 8.0–9.0), 50 mM glycine-NaOH buffer (pH 9.0–10.0) and 50 mM CAPS buffer (pH 10.0–11.0).

(6) Thermal stability:

The present enzyme was found to be stable at a temperature up to about 45° C. as shown in Table 4 in which the present enzyme was treated at each temperature for 30 min. in 50 mM Tris-HCl buffer (pH 7.5).

(7) Enzyme activity measurement:

The enzyme activity forming 1 μM yellow pigment in 1 minute under the following conditions is referred to as 1 U of the present enzyme.

PREPARATION OF REAGENTS

Solution 1 (the substrate solution)

6.63 g of creatine is dissolved in 500 ml of 50 mM buffer, pH 7.7.

Solution 2 (the coloring solution)

10 p-dimethylaminobenzaldehyde is dissolved in 500 ml special grade ethanol and then mixed with a mixture of 575 ml ion-exchanged water and 75 ml conc. hydrochloric acid.

Measurement procedures 1) 0.9 ml of the solution 1 is pre-incubated at 37° C. for 5 min.
2) 0.1 ml of an enzyme solution (adjusted in the range of approx. 1–2 U/ml) is mixed therewith and allowed to react at 37° C. for 10 min.
3) After 10 min. reaction, 2 ml of the solution 2 is mixed therewith.
4) After being mixed with the solution 2, the mixture is allowed to stand at 25° C. for 20 min., and the absorbance at 435 nm is determined (the OD sample).
5) For the blank sample, 0.9 ml of the solution 1 is incubated at 37° C. for 10 min., and 2 ml of the solution 2 is mixed therewith, followed by addition of 0.1 ml of an enzyme solution thereto. The mixture is allowed to stand at 25° C. for 20 min. and the absorbance at 435 nm is then determined (the OD blank sample).

Activity calculation

U/ml = ΔOD × 18.06* × degree of dilution (* the coefficient calculated from a urea calibration curve)

(8) Inhibitors:

The present enzyme was strongly inhibited by $AgNO_3$, $HgCl_2$, and $CuSO_4$, respectively, as shown Table 1 in which the effect of each metal salt was determined by adding it to the reaction solution.

TABLE 1

| inhibitor | Effect of Inhibitor | |
|---|---|---|
| | final conc. (mM) | relative activity (%) |
| (added to the substrate) | | |
| none | 0 | 100 |
| $AgNO_3$ | 1 | 1 |
| $HgCl_2$ | 1 | 1.9 |
| $CuSO_4$ | 1 | 3.3 |
| (added to the enzyme solution) | | |
| none | 0 | 100 |
| $AgNO_3$ | 1 | 1 |
| $HgCl_2$ | 1 | 1.7 |
| $CuSO_4$ | 1 | 3.4 |

(9) Km value:

Km value of $1.3 \times 10^{-2}$ M determined by Lineweaver-Burk plot (creatine substrate, pH 7.7, 37° C.).

(10) Molecular weight:

80,000 ± 5000 determined by gel filtration on TSK gel G3000SWXL.

EXAMPLES

The present invention is described in more detail with reference to the following examples, which however are not intended to limit the scope of the invention.

Example 1

100 ml of a medium (pH 6.7) consisting of 1.6% creatine, 2.0% polypeptone, 0.8% yeast extract, 0.03% $KH_2PO_4$, 0.07% $K_2HPO_4$, 0.02% $MgSO_4 \cdot 7H_2O$, 0.02% $MnSO_4 \cdot 4H_2O$, and tap water was introduced to a Sakaguchi flask and sterilized at 120° C. for 10 min. After the initial pH was confirmed, Alkaligenes sp. KS-85 (FERM BP-4487) from a storage slant was inoculated thereonto. The microorganism was cultured under shaking at 30° C. for about 24 hours. This culture, 100 ml (the content of 1 Sakaguchi flask), was transferred to 30-liter jar containing 20 liters of a medium adjusted to pH 6.7, prepared and sterilized in the same manner as described above. The microorganism was cultured at 30° C. for about 24 hours at 450 rpm while air was passed at 20 liters/min.

After conclusion of the culture, the microorganism was collected from 20 liters of the culture by means of microza (PW-303, a product of Asahi Kasei Co., Ltd.), washed with 20 mM phosphate buffer, pH 7.5, and suspended in about 10 liters of the buffer.

Step 1 (preparation of a crude enzyme solution)

To the above bacterial suspension (10 liters) were added 20 g lysozyme (100 ml of 50 mM phosphate buffer, pH 8.0) and 1 liter of 0.55M EDTA, pH 8.0, followed by being mixed, and the mixture was allowed to stand at 30° C. overnight. Then, 500 ml of 5% aq. protamine, pH 8.0, was added dropwise thereto with stirring for removal of nucleic acids. The supernatant was introduced into an ultrafiltration membrane and dialyzed against 10 mM CAPS-NaOH buffer, pH 10.0 (hereinafter referred to as "buffer A").

Step 2 (DEAE-cellulose)

About 9 kg (wet weight) of DEAE-cellulose was introduced to about 28 liters of the above dialyzed solution, followed by being mixed so that the present enzyme was adsorbed onto the resin. The DEAE-cellulose resin was washed with the buffer A containing 5% glycerin and 0.005% 2-mercaptoethanol. Then, the present enzyme was eluted therefrom with the buffer A containing 0.5M KCl and concentrated by ultrafiltration.

Step 3 (DEAE-sepharose CL-4B)

About 1.0 kg (wet weight) of DEAE-cellulose CL-4B equilibrated with the buffer A was added to the concentrate (about 1 liter) obtained in Step 2 and was then stirred so that the present enzyme was adsorbed onto the resin. The DEAE-sepharose CL-4B resin was washed with the buffer A containing 0.05M KCl, and the present enzyme was eluted with the buffer A and then concentrated by ultrafiltration.

Step 4 (Sephacryl S-200)

Approx. 1 liter of the concentrate obtained in Step 3 was fractionated by molecular sieve through a Sephacryl S-200 column to give 2.2 g active fraction. The active fraction had a specific activity of 9.0 U/OD 280 nm.

Example 2

To demonstrate the superiority of the present enzyme over conventional one in reactivity and substrate specificity, the present enzyme and the conventional creatine amidinohydrolase (CRH-211, a product of Toyobo Co., Ltd.) were allowed to react in a predetermined amount respectively with a predetermined amount of the substrate, and the reaction was monitored with time for comparison of the two enzymes. In this measurement, creatine was decomposed by creatine amidinohydrolase to form sarcosine which was then decomposed by sarcosine oxidase to form hydrogen peroxide, and the hydrogen peroxide was colored by a coloring reagent and then quantitatively determined by its absorbance at 510 nm. The creatine substrate used herein was so dilute that the creatine was completely decomposed in the reaction for 10–20 min. during which the absorbance at OD 510 nm reached a constant value. In this measurement, a shorter period of time elapsed before the absorbance at OD 510 nm reaches a constant value indicates the superiority of the enzyme in reactivity and substrate specificity.

1. Preparation of reagents

Table 2 shows the reagents used in this example, along with the concentrations thereof.

TABLE 2

| reagents | concentration |
| --- | --- |
| creatine substrate solution[1] | 10 mg/dl |
| 2,4-dichlorophenol[2] | 2% |
| 4-aminoantipyrine[2] | 70 mg/dl |
| sarcosine oxidase[2] | 30 U/ml |
| peroxidase[2] | 70 U/ml |
| creatine amidinohydrolase[3] | 20 U/ml |

[1] dissolved in 50 mM phosphate buffer, pH 7.7.
[2] dissolved in 50 mM phosphate buffer, pH 8.0.
[3] The enzyme prepared in Example 1 was adjusted to the exact concentration.

2. Measurement Method 0.2 ml of the creatine substrate solution, 0.1 ml of 2,4-dichlorophenol, 0.1 ml of 4-aminoantipyrine, 0.4 ml of sarcosine oxidase, and 0.2 ml of peroxidase were mixed and incubated at 37° C. for 3 min. Then, 1 ml of the creatine amidinohydrolase (20 U/ml) was added thereto, and the mixture was allowed to stand for 15 sec. The sample was then monitored for its OD 510 nm at an interval of 30 seconds at 37° C. with a spectrophotometer (Hitachi U-2000).

Figure 5:
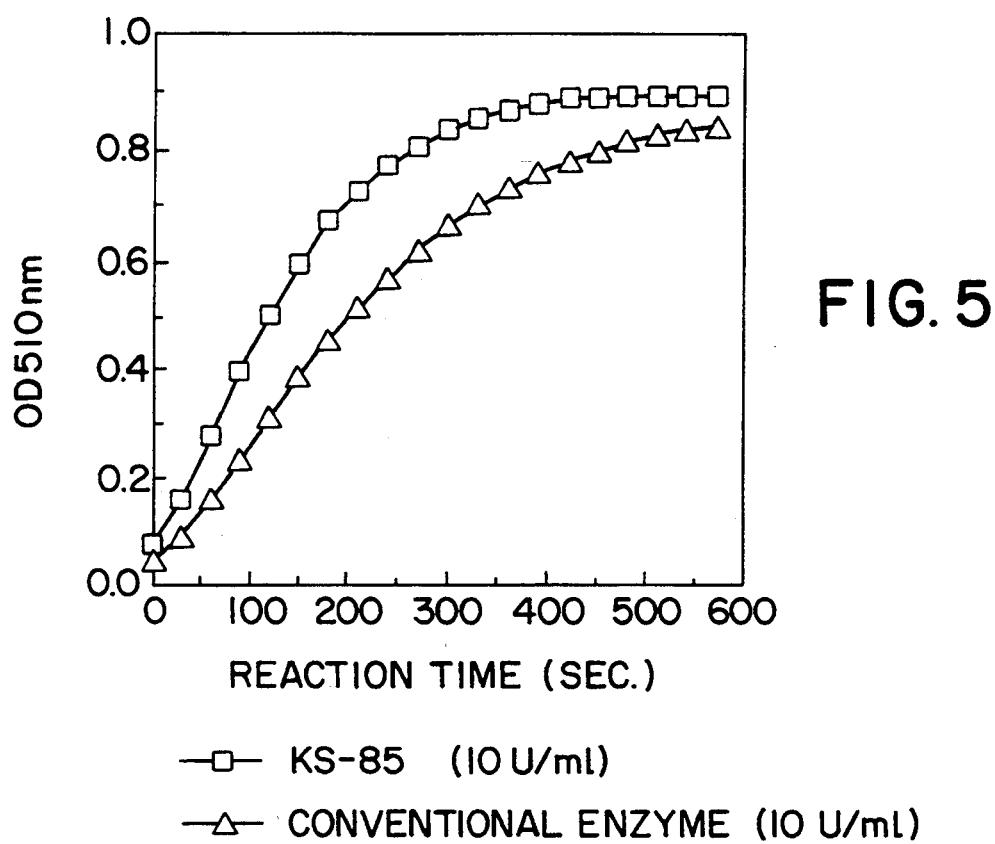
FIG. 5 is a graphic depiction of a process monitored with time to show the difference in substrate specificity and reactivity between the present enzyme and the conventional enzyme, in which a predetermined amount of the substrate is decomposed with a predetermined amount of the enzyme. This figure depicts enzyme reaction with time based on a $Km=2.4\times10^{-2}M$ in the case of the conventional enzyme and the concentration of the substrate in the reaction solution of 100 mg/l under measurement conditions of 1 mM phosphate buffer, pH 7.7 at 37° C. for 10 minutes using a measurement method of monitoring hydrogen peroxide at 510 nm increased with time at 37° C. for 10 minutes in the POD-SOD-coupled reaction.

As shown in FIG. 5. the present enzyme reached a constant value for 400 seconds in the reaction, whereas the conventional creatine amidinohydrolase did not reach a constant value even for 600 seconds in the reaction. This result indicates the superiority of the present enzyme over the conventional creatine amidinohydrolase in respect of the substrate specificity and reactivity with the substrate.

We claim:

1. A creatine amidinohydrolase isolated from Alkaligenes sp. KS-85 FERM BP-4487 having the following physicochemical properties:
    (a) action: hydrolysis of 1 mole of creatine to form 1 mole of sarcosine and 1 mole of urea;
    (b) substrate specificity: specific for a creatine substrate;
    (c) optimum pH: 7–9;
    (d) optimum temperature: about 35°–45° C.;
    (e) pH stability: stable in the range of pH 5.0–10.5 at 25° C. for 17 hours;
    (f) thermal stability: stable at a temperature up to about 45° C. at pH 7.5 for 30 min.;
    (g) inhibitors: $AgNO_3$, $HgCl_2$, $CuSO_4$, etc.; and
    (h) molecular weight: about 80,000±5000 as determined by gel filtration.

2. A process for producing the creatine amidinohydrolase of claim 1 by culturing Alkaligenes sp. KS-85 FERM BP-4487 and isolating said creatine amidinohydrolase from the culture.

* * * * *